US009274102B2

(12) United States Patent
Namba et al.

(10) Patent No.: US 9,274,102 B2
(45) Date of Patent: Mar. 1, 2016

(54) METHOD OF SCREENING FOR AN INHIBITOR OF ODOR CAUSE BY FURANEOL

(71) Applicant: Kao Corporation, Chuo-ku, Tokyo (JP)

(72) Inventors: Aya Namba, Katsushika-ku (JP); Naoko Saito, Utsunomiya (JP); Michiaki Inoue, Cincinnati, OH (US); Tsuyoshi Toyabe, Funabashi (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 14/519,958

(22) Filed: Oct. 21, 2014

(65) Prior Publication Data
US 2015/0111229 A1 Apr. 23, 2015

(30) Foreign Application Priority Data

Oct. 22, 2013 (JP) .................................. 2013-219336

(51) Int. Cl.
*G01N 33/50* (2006.01)
(52) U.S. Cl.
CPC .................................. *G01N 33/5044* (2013.01)
(58) Field of Classification Search
CPC ............ A61K 39/39533; G01N 33/50; G01N 2500/04; G01N 2500/10
See application file for complete search history.

(56) References Cited

U.S. PATENT DOCUMENTS

| 2013/0210022 A1 | 8/2013 | Kato et al. |
| 2013/0210775 A1 | 8/2013 | Kato et al. |
| 2014/0186864 A1 | 7/2014 | Kato et al. |
| 2015/0110669 A1 | 4/2015 | Namba et al. |
| 2015/0110731 A1 | 4/2015 | Namba et al. |

FOREIGN PATENT DOCUMENTS

| JP | 2012-250958 A | 12/2012 |
| JP | 2015-081237 A | 4/2015 |
| JP | 2015-202075 A | 11/2015 |
| JP | 2015-202076 A | 11/2015 |
| JP | 2015-202077 A | 11/2015 |
| WO | WO 2009/078360 A1 | 6/2009 |
| WO | WO 2012/169644 A1 | 12/2012 |

OTHER PUBLICATIONS

Indo, M., Synthetic Flavor and Fragrance, Enlarged and Revised Edition, 2005, The Chemical Daily Co., Ltd., Tokyo, Japan, pp. 348-349.
Cutzach, I et al., "Identification of volatile compounds with a 'toasty' aroma in heated oak used in barrelmaking," J Agric Food Chem, Jun. 1997, 45: 2217-2224, Am. Chem Soc, Washington, DC.
Karagül-Yüceer, Y et al., "Aroma characterization of fresh and stored-nonfat dry milk," Chapter 8 in Freshness and Shelf Life of Foods, ACS Symposium Series vol. 836, Keith R. Cadwallader et al., eds., Oct. 2002, pp. 108-123, Am. Chem. Soc, Washington, DC.
Botelho, G et al., "Characterisation of free and glycosidically bound odourant compounds of Aragonez clonal musts by GC-O," Anal Chim Acta, Jan. 2010; 657(2): 198-203, Elsevier, Amsterdam, Netherlands.
Excerpted file history of U.S. Appl. No. 14/519,962, filed Oct. 21, 2014: Non-final office action mailed Nov. 25, 2015 by the United States Patent and Trademark Office, Alexandria, VA.

*Primary Examiner* — Robert Landsman
(74) *Attorney, Agent, or Firm* — Sterne, Kessler, Goldstein & Fox P.L.L.C.

(57) ABSTRACT

It is intended to identify a substance inhibiting an odor caused by 2,5-dimethyl-4-hydroxy-3(2H)-furanone. The present invention provides a method for searching for an inhibitor of an odor caused by 2,5-dimethyl-4-hydroxy-3(2H)-furanone, comprising: adding a test substance and 2,5-dimethyl-4-hydroxy-3(2H)-furanone to an olfactory receptor OR5K1 or a polypeptide having at least 80% amino acid sequence identity thereto; measuring the response of the olfactory receptor or the polypeptide to 2,5-dimethyl-4-hydroxy-3(2H)-furanone; and identifying a test substance inhibiting the response of the olfactory receptor or the polypeptide, on the basis of the measured response.

11 Claims, 2 Drawing Sheets

SEQUENCE LISTING

```
<160> NUMBER OF SEQ ID NOS: 8

<210> SEQ ID NO 1
<211> LENGTH: 927
<212> TYPE: DNA
<213> ORGANISM: Homo sapiens
<220> FEATURE:
<223> OTHER INFORMATION: DNA encoding human OR5K1

<400> SEQUENCE: 1
atggctgaag aaaatcatac catgaaaaat gagtttatcc tcacaggatt tacagatcac      60
cctgagctga agactctgct gtttgtggtg ttctttgcca tctatctgat caccgtggtg     120
gggaatatta gtttggtggc actgatattt acacaccgtc ggcttcacac accaatgtac     180
atctttctgg gaaatctggc tcttgtggat tcttgctgtg cctgtgctat tacccccaaa     240
atgttagaga acttcttttc tgagaacaaa aggatttccc tctatgaatg tgcagtacag     300 tttattttc tttgcactgt ggaaactgca gactgctttc ttctggcagc aatggcctat     360
gaccgctatg tggccatatg caacccactg cagtaccaca tcatgatgtc caagaaactc     420
```

```
tgcattcaga tgaccacagg ggccttcata gctggaaacc tgcattccat gattcatgta    480
gggcttgtat ttaggttagt tttctgtgga tcgaatcaca tcaaccactt ttactgtgat    540
attcttccct tgtatagact ctcttgtgtt gatccttata tcaatgaact ggttctattc    600
atcttctcag gttcagttca agtctttacc ataggtagtg tcttaatatc ttatctctat    660
attcttctta ctattttcaa aatgaaatcc aaagagggaa gggccaaagc ttttctacc    720 tgtgcatccc acttttgtc agtttcatta ttctatggat ctcttttctt catgtacgtt    780
agaccaaatt tgcttgaaga aggggataaa gatataccag ctgcaatttt atttacaata    840
gtagttccct tactaaatcc tttcatttat agcctgagaa atagggaagt aataagtgtc    900
ttaagaaaaa ttctgatgaa gaaataa                                        927
```

<210> SEQ ID NO 2
<211> LENGTH: 308
<212> TYPE: PRT
<213> ORGANISM: Homo sapiens
<220> FEATURE:
<223> OTHER INFORMATION: Polypeptide of human OR5K1

<400> SEQUENCE: 2

```
Met Ala Glu Glu Asn His Thr Met Lys Asn Glu Phe Ile Leu Thr Gly
1               5                   10                  15

Phe Thr Asp His Pro Glu Leu Lys Thr Leu Leu Phe Val Val Phe Phe
                20                  25                  30

Ala Ile Tyr Leu Ile Thr Val Val Gly Asn Ile Ser Leu Val Ala Leu
            35                  40                  45

Ile Phe Thr His Arg Arg Leu His Thr Pro Met Tyr Ile Phe Leu Gly
        50                  55                  60

Asn Leu Ala Leu Val Asp Ser Cys Cys Ala Cys Ala Ile Thr Pro Lys
65                  70                  75                  80

Met Leu Glu Asn Phe Phe Ser Glu Asn Lys Arg Ile Ser Leu Tyr Glu
                85                  90                  95

Cys Ala Val Gln Phe Tyr Phe Leu Cys Thr Val Glu Thr Ala Asp Cys
            100                 105                 110

Phe Leu Leu Ala Ala Met Ala Tyr Asp Arg Tyr Val Ala Ile Cys Asn
        115                 120                 125

Pro Leu Gln Tyr His Ile Met Met Ser Lys Lys Leu Cys Ile Gln Met
    130                 135                 140

Thr Thr Gly Ala Phe Ile Ala Gly Asn Leu His Ser Met Ile His Val
145                 150                 155                 160

Gly Leu Val Phe Arg Leu Val Phe Cys Gly Ser Asn His Ile Asn His
                165                 170                 175

Phe Tyr Cys Asp Ile Leu Pro Leu Tyr Arg Leu Ser Cys Val Asp Pro
            180                 185                 190

Tyr Ile Asn Glu Leu Val Leu Phe Ile Phe Ser Gly Ser Val Gln Val
        195                 200                 205

Phe Thr Ile Gly Ser Val Leu Ile Ser Tyr Leu Tyr Ile Leu Leu Thr
    210                 215                 220

Ile Phe Lys Met Lys Ser Lys Glu Gly Arg Ala Lys Ala Phe Ser Thr
225                 230                 235                 240

Cys Ala Ser His Phe Leu Ser Val Ser Leu Phe Tyr Gly Ser Leu Phe
                245                 250                 255

Phe Met Tyr Val Arg Pro Asn Leu Leu Glu Glu Gly Asp Lys Asp Ile
            260                 265                 270
```

```
Pro Ala Ala Ile Leu Phe Thr Ile Val Val Pro Leu Leu Asn Pro Phe
            275                 280                 285

Ile Tyr Ser Leu Arg Asn Arg Glu Val Ile Ser Val Leu Arg Lys Ile
            290                 295                 300

Leu Met Lys Lys
305

<210> SEQ ID NO 3
<211> LENGTH: 684
<212> TYPE: DNA
<213> ORGANISM: Homo sapiens
<220> FEATURE:
<223> OTHER INFORMATION: DNA encoding human RTP1S

<400> SEQUENCE: 3
atgtgtaaaa gcgtgaccac agatgagtgg aagaaagtct tctatgagaa gatggaggag      60
gcaaagccgg ctgacagctg ggacctcatc atagacccca acctcaagca caatgtgctg     120
agccctggtt ggaagcagta cctggaattg catgcttcag caggttccac ctgctcctgg     180
tgctggcaca cctggcagtc gccctacgtg gtcatcctct tccacatgtt cctggaccgc     240
gcccagcggg cgggctcggt gcgcatgcgc gtcttcaagc agctgtgcta tgagtgcggc     300
acggcgcggc tggacgagtc cagcatgctg gaggagaaca tcgagggcct ggtggacaac     360
ctcatcacca gcctgcgcga gcagtgctac ggcgagcgtg gcggccagta ccgcatccac     420
gtggccagcc gccaggacaa ccggcggcac cgcggagagt tctgcgaggc ctgccaggag     480
ggcatcgtgc actggaagcc cagcgagaag ctgctggagg aggaggcgac cacctacacc     540
ttctcccggg cgcccagccc caccaagtcg caggaccaga cgggctcagg ctggaacttc     600
tgctctatcc cctggtgctt gttttgggcc acggtcctgc tgctgatcat ctacctgcag     660
ttctctttcc gtagctccgt ataa                                             684

<210> SEQ ID NO 4
<211> LENGTH: 227
<212> TYPE: PRT
<213> ORGANISM: Homo sapiens
<220> FEATURE:
<223> OTHER INFORMATION: Polypeptide of human RTP1S

<400> SEQUENCE: 4

Met Cys Lys Ser Val Thr Thr Asp Glu Trp Lys Lys Val Phe Tyr Glu
1               5                   10                  15

Lys Met Glu Glu Ala Lys Pro Ala Asp Ser Trp Asp Leu Ile Ile Asp
            20                  25                  30

Pro Asn Leu Lys His Asn Val Leu Ser Pro Gly Trp Lys Gln Tyr Leu
        35                  40                  45

Glu Leu His Ala Ser Gly Arg Phe His Cys Ser Trp Cys Trp His Thr
    50                  55                  60

Trp Gln Ser Pro Tyr Val Val Ile Leu Phe His Met Phe Leu Asp Arg
65                  70                  75                  80

Ala Gln Arg Ala Gly Ser Val Arg Met Arg Val Phe Lys Gln Leu Cys
                85                  90                  95

Tyr Glu Cys Gly Thr Ala Arg Leu Asp Glu Ser Ser Met Leu Glu Glu
            100                 105                 110

Asn Ile Glu Gly Leu Val Asp Asn Leu Ile Thr Ser Leu Arg Glu Gln
        115                 120                 125

Cys Tyr Gly Glu Arg Gly Gly Gln Tyr Arg Ile His Val Ala Ser Arg
    130                 135                 140
```

Gln Asp Asn Arg Arg His Arg Gly Glu Phe Cys Glu Ala Cys Gln Glu
145                 150                 155                 160

Gly Ile Val His Trp Lys Pro Ser Glu Lys Leu Leu Glu Glu Glu Ala
            165                 170                 175

Thr Thr Tyr Thr Phe Ser Arg Ala Pro Ser Pro Thr Lys Ser Gln Asp
            180                 185                 190

Gln Thr Gly Ser Gly Trp Asn Phe Cys Ser Ile Pro Trp Cys Leu Phe
        195                 200                 205

Trp Ala Thr Val Leu Leu Leu Ile Ile Tyr Leu Gln Phe Ser Phe Arg
    210                 215                 220

Ser Ser Val
225

<210> SEQ ID NO 5
<211> LENGTH: 678
<212> TYPE: DNA
<213> ORGANISM: Homo sapiens
<220> FEATURE:
<223> OTHER INFORMATION: DNA encoding human RTP2

<400> SEQUENCE: 5
atgtgtacca gcttgaccac ttgtgagtgg aagaaagtct tctatgagaa gatggaggtg      60
gcaaagccag cggacagctg ggagctcatc atagacccca acctcaagcc cagtgagctg     120 gccccctggct ggaagcagta cctggagcag cacgcctcag gcaggttcca ctgctcctgg     180
tgctggcaca cctggcagtc tgcccatgtg gtcatcctct ccacatgtt cctggaccgc      240 gcccagcggg cgggctcggt gcgcatgcgc gtcttcaagc agctgtgcta tgagtgcggc     300
acggcgcggc tggacgagtc cagcatgctg gaggagaaca tcgagggcct ggtgacaaac     360
ctcatcacca gcctgcgcga gcagtgctac gaggaggatg tggccagta ccgcatccac      420 gtggccagcc gcccggacag cgggccgcat cgtgcagagt ctgtgaggc ctgccaggag      480 ggcatcgttc actggaagcc cagcgagaag ctgctggagg aggaggtgac cacctacacc     540
tctgaagcct ccaagccgag ggcccaggcg ggatccggct acaacttctt gtctcttcgc     600
tggtgcctct tctgggcctc tctctgcctg ctcgttgttt acctgcagtt ctccttcctc     660
agtcctgcct tcttttag                                                    678

<210> SEQ ID NO 6
<211> LENGTH: 225
<212> TYPE: PRT
<213> ORGANISM: Homo sapiens
<220> FEATURE:
<223> OTHER INFORMATION: Polypeptide of human RTP2

<400> SEQUENCE: 6

Met Cys Thr Ser Leu Thr Thr Cys Glu Trp Lys Lys Val Phe Tyr Glu
1               5                   10                  15

Lys Met Glu Val Ala Lys Pro Ala Asp Ser Trp Glu Leu Ile Ile Asp
            20                  25                  30

Pro Asn Leu Lys Pro Ser Glu Leu Ala Pro Gly Trp Lys Gln Tyr Leu
        35                  40                  45

Glu Gln His Ala Ser Gly Arg Phe His Cys Ser Trp Cys Trp His Thr
    50                  55                  60

Trp Gln Ser Ala His Val Val Ile Leu Phe His Met Phe Leu Asp Arg
65                  70                  75                  80

Ala Gln Arg Ala Gly Ser Val Arg Met Arg Val Phe Lys Gln Leu Cys

```
                    85                  90                  95
Tyr Glu Cys Gly Thr Ala Arg Leu Asp Glu Ser Ser Met Leu Glu Glu
                100                 105                 110

Asn Ile Glu Gly Leu Val Asp Asn Leu Ile Thr Ser Leu Arg Glu Gln
            115                 120                 125

Cys Tyr Glu Glu Asp Gly Gly Gln Tyr Arg Ile His Val Ala Ser Arg
        130                 135                 140

Pro Asp Ser Gly Pro His Arg Ala Glu Phe Cys Glu Ala Cys Gln Glu
145                 150                 155                 160

Gly Ile Val His Trp Lys Pro Ser Glu Lys Leu Leu Glu Glu Glu Val
                165                 170                 175

Thr Thr Tyr Thr Ser Glu Ala Ser Lys Pro Arg Ala Gln Ala Gly Ser
                180                 185                 190

Gly Tyr Asn Phe Leu Ser Leu Arg Trp Cys Leu Phe Trp Ala Ser Leu
            195                 200                 205

Cys Leu Leu Val Val Tyr Leu Gln Phe Ser Phe Leu Ser Pro Ala Phe
        210                 215                 220

Phe
225

<210> SEQ ID NO 7
<211> LENGTH: 681
<212> TYPE: DNA
<213> ORGANISM: Homo sapiens
<220> FEATURE:
<223> OTHER INFORMATION: DNA encoding polypeptide of recombinant human
      RTP1S

<400> SEQUENCE: 7
atgtgcaagt ccctgacaac gggagagtgg aagaagatct tctacgagaa aatggaggag      60
gtgaaacccg cagactcctg ggacctgatc atggatccca acctccagca taacgtattg     120 gccccggat ggaagcagta cctggagcag cacgcctctg gccgcttcca ctgctcctgg      180
tgctggcata gctggcagtc ctcccaactg gtgatcctct ccacatgta cctggataag      240 acccagcgga cgggctgcgt gcgcatgaga gtcttcaagc agctctgcta cgagtgtggc     300
tcctcccggc tggacgagtc gtccatgctg aggagaaaca tagagggct ggtggacaac     360 ctcgtctgca gcctccggga gcagtgctac ggggagaatg ggggacagta ccgcatccac     420
gtggcctccc gccaagacca ccagcgccac cggggagagt tctgcgaggc ctgccgcctg     480
ggcatcaccc actggaagcc cacggagaag atgctagagg aggaggcctc cacctacacc     540
ttctcccggc ctgcgaatcc ttccaagaca gccgactcgg gtttcagctg tgacttctgc     600
tccctccctt ggtgtatgtt ctgggccacg gtgctcttgc tcatcatata cctgcagatc     660
tccttcggca accctgtcta a                                                681

<210> SEQ ID NO 8
<211> LENGTH: 226
<212> TYPE: PRT
<213> ORGANISM: Homo sapiens
<220> FEATURE:
<223> OTHER INFORMATION: Polypeptide of recombinant human RTP1S

<400> SEQUENCE: 8

Met Cys Lys Ser Leu Thr Thr Gly Glu Trp Lys Lys Ile Phe Tyr Glu
1               5                   10                  15

Lys Met Glu Glu Val Lys Pro Ala Asp Ser Trp Asp Leu Ile Met Asp
            20                  25                  30
```

-continued

```
Pro Asn Leu Gln His Asn Val Leu Ala Pro Gly Trp Lys Gln Tyr Leu
        35              40              45
Glu Gln His Ala Ser Gly Arg Phe His Cys Ser Trp Cys Trp His Ser
    50              55              60
Trp Gln Ser Ser Gln Leu Val Ile Leu Phe His Met Tyr Leu Asp Lys
65              70              75              80
Thr Gln Arg Thr Gly Cys Val Arg Met Arg Val Phe Lys Gln Leu Cys
            85              90              95
Tyr Glu Cys Gly Ser Ser Arg Leu Asp Glu Ser Ser Met Leu Glu Glu
            100             105             110
Asn Ile Glu Gly Leu Val Asp Asn Leu Val Cys Ser Leu Arg Glu Gln
        115             120             125
Cys Tyr Gly Glu Asn Gly Gly Gln Tyr Arg Ile His Val Ala Ser Arg
    130             135             140
Gln Asp His Gln Arg His Arg Gly Glu Phe Cys Glu Ala Cys Arg Leu
145             150             155             160
Gly Ile Thr His Trp Lys Pro Thr Glu Lys Met Leu Glu Glu Glu Ala
            165             170             175
Ser Thr Tyr Thr Phe Ser Arg Pro Ala Asn Pro Ser Lys Thr Ala Asp
            180             185             190
Ser Gly Phe Ser Cys Asp Phe Cys Ser Leu Pro Trp Cys Met Phe Trp
        195             200             205
Ala Thr Val Leu Leu Leu Ile Ile Tyr Leu Gln Ile Ser Phe Gly Asn
    210             215             220
Pro Val
225
```

METHOD OF SCREENING FOR AN INHIBITOR OF ODOR CAUSE BY FURANEOL

REFERENCE TO SEQUENCE LISTING SUBMITTED ELECTRONICALLY

The content of the electronically submitted substitute sequence listing, file name 2537_1030000_SequenceListing_ST25.txt, size 13,719 bytes; and date of creation Oct. 10, 2014, filed herewith, is incorporated herein by reference in its entirety.

FIELD OF THE INVENTION

The present invention relates to a method for searching for an inhibitor of an odor caused by Furaneol.

BACKGROUND OF THE INVENTION

A large number of malodorous molecules differing in polarity or molecular weight are found in our living environments. Various deodorization methods have been developed so far in order to deodorize these diverse malodorous molecules. In general, such deodorization methods are broadly classified into biological methods, chemical methods, physical methods, and sensory methods. Among the malodorous molecules, highly polar short-chain fatty acids or amines can be deodorized by the chemical method, i.e., neutralization reaction. Sulfur compounds such as thiol can be deodorized by the physical method, i.e., adsorption treatment. Still, there remain a large number of malodorous molecules which cannot be dealt with by the conventional deodorization methods. Also, the deodorization method based on adsorption treatment has a problem that it tends to cause the re-emission of a bad smell. In addition, these conventional methods may mask even odors other than the bad smell of interest. Thus, a deodorization method which can overcome these problems has been demanded.

Another known method involves deodorizing a bad smell by rendering a different odor more strongly perceivable using a fragrance. In this method, however, the odor of the fragrance may cause discomfort. In addition, an odorous substance which exhibits an effective deodorizing effect on the malodorous substance of interest must be searched for in order to mask the bad smell by a different odor of a perfume, a fragrance, or the like. Heretofore, sensory tests by experts have been conducted for the evaluation of odors. Such sensory tests, however, has problems such as the need of fostering experts capable of evaluating odors and low throughputs. Thus, the previous search for an odorous substance which exhibits a deodorizing effect has not been easy to achieve.

In mammals such as humans, the sense of smell works by the mechanism where odor molecules bind to olfactory receptors on olfactory nerve cells present in the olfactory epithelium located in the upper region of the nasal cavity to transmit the responses of the receptors thereto to the central nervous system. In humans, approximately 400 olfactory receptors have been reported, and genes encoding these receptors account for approximately 3% of all human genes. In general, a set of olfactory receptors is associated with a set of odor molecules. This means that individual olfactory receptors can respond to a plurality of structurally similar odor molecules with different affinities, while individual odor molecules can be recognized by a plurality of olfactory receptors. According to another report, an odor molecule activating a certain olfactory receptor functions as an antagonist inhibiting the activation of a different olfactory receptor. These combined responses of a set of olfactory receptors render individual odors perceivable.

Accordingly, when a certain odor molecule coexists with a different odor molecule, the different odor molecule may inhibit the response of a receptor corresponding to the certain odor molecule, resulting in the final perception of a different odor. Such a mechanism is called the antagonism of an olfactory receptor. The alteration of an odor caused by this receptor antagonism is a preferred deodorization approach because this approach, unlike the deodorization methods which involve adding another odor of, for example, a perfume, and fragrance can specifically cancel the perception of a bad smell and does not cause discomfort derived from such a fragrance.

Skin tanning agents (also called self-tanning agents or sunless tanning agents) are skin cosmetics which colors the skin. Mainly, dihydroxyacetone (DHA) is used alone or in combination with erythrulose or the like as an ingredient which causes the skin color to turn brown. Such an ingredient reacts with the upper layer of the skin to color the skin brown. Although this coloring is believed to proceed through browning reaction, the details of a mechanism underlying this reaction have hardly been elucidated. The browning reaction is also called Maillard reaction in the field of food chemistry. This term refers to the reaction through which a nitrogen-containing compound such as an amino acid or a protein is polymerized with a reduced sugar to form a brown polymer called melanoidin. The Maillard reaction is involved in food coloring or aroma component formation caused by the heating, etc. of foods.

2,5-Dimethyl-4-hydroxy-3(2H)-furanone (Furaneol) is a substance known to have an odor expressed as a "strong fruity caramel aroma", a "burnt caramel aroma", "burnt sugar", a "curry-like flavor", a "cotton candy smell", etc. (Non-Patent Documents 1 to 4). Patent Document 1 describes a beer-tasted beverage having a taste and flavor or a fragrant smell enhanced by the formation of maltol and Furaneol in a fermentation undiluted solution.

CITATION LIST

Patent Document

[Patent Document 1] WO 2009/078360

Non-Patent Document

[Non-Patent Document 1] Gosei Koryo—Kagaku To Shohin Chishiki—(Synthetic Flavor and Fragrance—Chemistry and Product Knowledge—in English), 2005, The Chemical Daily Co., Ltd.
[Non-Patent Document 2] J. Agric. Food Chem., 1997, 45 (6): 2217-2224
[Non-Patent Document 3] ACS Symp Ser., 2002, 836: 108-123
[Non Patent Document 4] Anal Chim Acta., 2010, 657 (2): 198-203

SUMMARY OF INVENTION

The present invention provides:
a method for searching for an inhibitor of an odor caused by 2,5-dimethyl-4-hydroxy-3(2H)-furanone (Furaneol), comprising:
adding a test substance and 2,5-dimethyl-4-hydroxy-3 (2H)-furanone (Furaneol) to an olfactory receptor OR5K1 or a polypeptide having at least 80% amino acid sequence identity thereto;

measuring the response of the olfactory receptor or the polypeptide to 2,5-dimethyl-4-hydroxy-3(2H)-furanone (Furaneol); and identifying a test substance inhibiting the response of the olfactory receptor or the polypeptide, on the basis of the measured response.

DETAILED DESCRIPTION OF THE INVENTION

Figure 1:
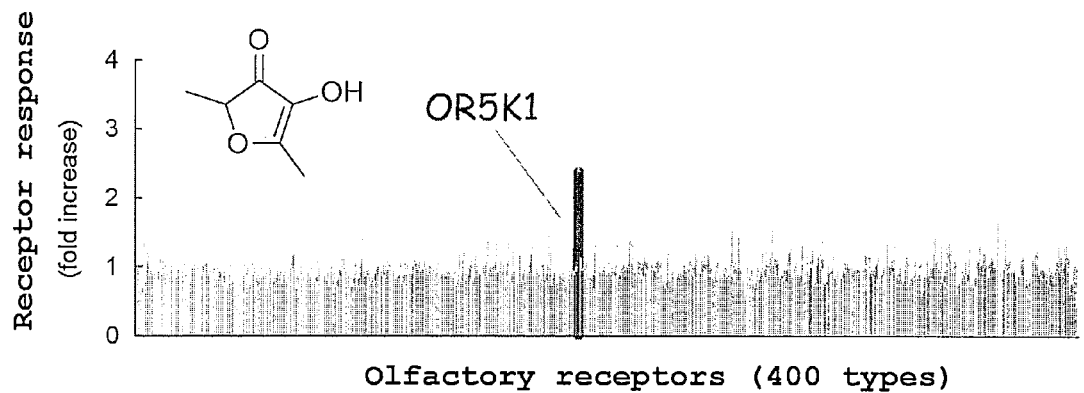
FIG. 1 shows the responses of olfactory receptors to Furaneol. The abscissa represents individual olfactory receptors. The ordinate represents response intensity.

The term "masking" in relation to odors as used herein refers to a general approach for canceling or weakening the perception of the odor of interest. The "masking" may include chemical approaches, physical approaches, biological approaches, and sensory approaches. Examples of the masking include: an arbitrary approach for removing an odor molecule causative of the odor of interest from the environment (e.g., adsorption and chemical decomposition of the odor molecule); an approach for preventing the odor of interest from being released to the environment (e.g., containment); and a method which involves adding a different odor of a flavor, a fragrance, or the like to reduce the perception of odor of interest.

The term "masking based on olfactory receptor antagonism" as used herein refers to one form of the above-mentioned "masking" in a broad sense. This approach utilizes both an odor molecule of the odor of interest and a different odor molecule to thereby inhibit a receptor response to the odor molecule of interest by the different odor molecule, resulting in change in odor which is perceived by individuals. The masking based on olfactory receptor antagonism is distinct from the approach of canceling the odor of interest by a different strong odor of a fragrance or the like, even though these approaches both employ the different odor molecule. One example of the masking based on olfactory receptor antagonism is the case of using a substance, such as an antagonist, which inhibits the response of an olfactory receptor. A substance inhibiting the response of a receptor to an odor molecule responsible for a particular odor can be applied to the receptor to thereby inhibit the response of the receptor to the odor molecule. The odor which is finally perceived by individuals can therefore be changed.

The term "Furaneol" as used herein refers to 2,5-dimethyl-4-hydroxy-3(2H)-furanone. The term "odor caused by Furaneol" can be an odor brought about by 2,5-dimethyl-4-hydroxy-3(2H)-furanone. The "odor caused by Furaneol" or the "odor caused by 2,5-dimethyl-4-hydroxy-3(2H)-furanone" as used herein can be typically expressed as, for example, a caramel aroma or a burnt sugar smell. Also, the "odor caused by Furaneol" or the "odor caused by 2,5-dimethyl-4-hydroxy-3(2H)-furanone" as used herein can be an unpleasant smell generated by the application of a conventional self-tanning agent to the skin, more specifically, an unpleasant smell expressed as a "burnt sugar smell" or the like generated by the application of a skin tanning agent containing dihydroxyacetone (DHA) to the skin.

The reported problem of commercially available skin tanning agents (self-tanning agents or sunless tanning agents) is their unique unpleasant smells expressed as earthy, burnt sugar smells, etc. upon application (D. M. Hindenlang and M. E. McDonnell, Cosmetics & Toiletries magazine, 2008, Vol. 123, No. 7, p. 67-74). Thus, improvement in the smells has been demanded. As a result of examining a cause of the unpleasant smell, 2,5-dimethyl-4-hydroxy-3(2H)-furanone (Furaneol) produced via methylglyoxal from dihydroxyacetone (DHA) contained in the skin tanning agents has been found to be a causative substance. For reducing such an unpleasant smell attributed to Furaneol, it has been required to control the odor of Furaneol.

The present inventors searched for an olfactory receptor which responds to Furaneol and successfully identified the receptor. The present inventor has also found that a substance inhibiting the response of the olfactory receptor can inhibit the perception of an odor caused by Furaneol by masking based on olfactory receptor antagonism. On the basis of these findings, the present inventor has found that a substance controlling an odor caused by Furaneol can be searched for with the response of the olfactory receptor as an index.

In the present specification, the sequence identity between nucleotide sequences or amino acid sequences is calculated according to the Lipman-Pearson method (Science, 1985, 227: 1435-41). Specifically, the sequence identity is calculated by analysis using the search homology program (Unit size to compare (ktup): 2) of genetic information processing software Genetyx-Win (Ver. 5.1.1; Software Development Co., Ltd.).

Figure 2:
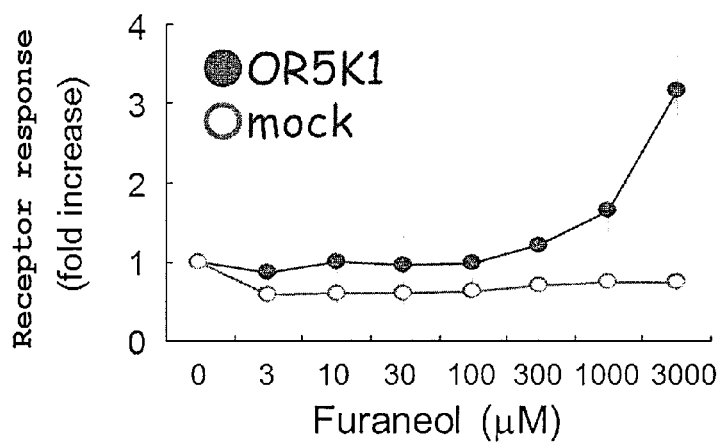
FIG. 2 shows the response of an olfactory receptor OR5K1 to varying concentrations of Furaneol. n=3, error bar=±SE.

As shown in FIG. 1, the present inventor identified an olfactory receptor OR5K1 as only one receptor responsive to Furaneol from among many olfactory receptors. OR5K1 is a novel receptor for Furaneol which has not been found so far to respond to Furaneol. As shown in FIG. 2, OR5K1 responds to Furaneol in a concentration-dependent manner. Thus, a substance inhibiting the response of OR5K1 can change the perception of an odor caused by Furaneol in the central nervous system by masking based on olfactory receptor antagonism, resulting in the selective inhibition of the odor caused by Furaneol.

According to the present invention, an inhibitor of an odor caused by Furaneol can be efficiently searched for. The inhibitor of an odor caused by Furaneol, identified by the present invention, can selectively deodorize the odor caused by Furaneol by masking based on olfactory receptor antagonism. Thus, the inhibitor of an odor caused by Furaneol, identified by the present invention can deodorize the odor caused by Furaneol, for example, an unpleasant smell generated upon application of conventional self-tanning agents (also called sunless tanning agents), without causing the problems such as discomfort derived from the odor of a fragrance in conventional deodorization methods using a deodorizer or a fragrance.

Thus, the present invention provides a method for searching for an inhibitor of an odor caused by Furaneol. This method comprises: adding a test substance and Furaneol to an olfactory receptor OR5K1; measuring the response of the olfactory receptor to Furaneol; and identifying a test substance inhibiting the response of the olfactory receptor, on the basis of the measured response. The identified test substance is selected as an inhibitor of an odor caused by Furaneol. The method of the present invention can be a method performed in vitro or ex vivo.

In the method of the present invention, a test substance and the odor causative substance Furaneol are added to an olfactory receptor OR5K1. A commercially available product (e.g., FURANEOL®; Nihon Firmenich K.K.) can be purchased and used as Furaneol.

The test substance used in the method of the present invention is not particularly limited as long as the substance is desired to be used as an inhibitor of an odor caused by Furaneol. The test substance may be a naturally occurring substance or may be a substance artificially synthesized by a chemical or biological method or the like. Alternatively, the test substance may be a compound, a composition, or a mixture.

The olfactory receptor OR5K1 used in the method of the present invention refers to an olfactory receptor expressed on a human olfactory cell and is registered as GI: 115270955 in GenBank. OR5K1 is encoded by a gene having the nucleotide sequence represented by SEQ ID NO: 1. This protein consists of the amino acid sequence represented by SEQ ID NO: 2.

In the method of the present invention, the olfactory receptor OR5K1 can be used in an arbitrary form unless the form loses responsiveness to Furaneol. For example, the olfactory receptor can be used in a form including: tissues or cells naturally expressing the olfactory receptor, such as an osmoreceptor or olfactory cells isolated from an organism, or cultures thereof; the membranes of olfactory cells carrying the olfactory receptor; recombinant cells genetically engineered to express the olfactory receptor, or cultures thereof; the membranes of the recombinant cells having the olfactory receptor; and artificial lipid bilayers having the olfactory receptor. These forms are all included in the scope of the olfactory receptor used in the present invention.

According to a preferred aspect, a cell naturally expressing the olfactory receptor, such as an olfactory cell, or a recombinant cell genetically engineered to express the olfactory receptor, or cultures of any of these cells are used as the olfactory receptor OR5K1. The recombinant cell can be prepared by the transformation of a cell with a vector having an insert of the gene encoding the olfactory receptor.

Preferably, a receptor-transporting protein (RTP) gene, together with the gene of the olfactory receptor, is transferred to the cell in order to promote the expression of the olfactory receptor on the cell membrane. Preferably, an RTP1S gene, more preferably RTP1S and RTP2 genes, together with the gene of the olfactory receptor, are transferred to the cell. Examples of RTP1S and RTP2 include human RTP1S and human RTP2, respectively. The human RTP1S is registered as GI: 50234917 in GenBank. This protein is encoded by a gene having the gene sequence represented by SEQ ID NO: 3 and consists of the amino acid sequence represented by SEQ ID NO: 4. The human RTP2 is registered as GI: 258547120 in GenBank. This protein is encoded by a gene having the gene sequence represented by SEQ ID NO: 5 and consists of the amino acid sequence represented by SEQ ID NO: 6.

Alternatively, a polypeptide which consists of an amino acid sequence having at least 78%, for example, 80% or higher, preferably 85% or higher, more preferably 90% or higher, still preferably 95% or higher, even more preferably 98% or higher, still even more preferably 99% or higher sequence identity to the amino acid sequence (SEQ ID NO: 4) of human RTP1S or the amino acid sequence (SEQ ID NO: 6) of human RTP2 and promotes the expression of the olfactory receptor on the cell membrane, as with human RTP1S or RTP2, may be used instead of the human RTP1S or RTP2. For example, a human RTP1S variant which is encoded by a gene having the gene sequence represented by SEQ ID NO: 7 and consists of the amino acid sequence represented by SEQ ID NO: 8 has 78.9% sequence identity to the amino acid sequence of human RTP1S represented by SEQ ID NO: 4 and has the function of promoting the expression of the olfactory receptor on the cell membrane. Alternatively, mouse RTP1S (Sci Signal., 2009, 2: ra9) also has 89% sequence identity to the amino acid sequence of human RTP1S represented by SEQ ID NO: 4 and has the function of promoting the expression of the olfactory receptor on the cell membrane. Such a human RTP1S variant and mouse RTP1S can be used instead of the human RTP1S in the preparation of the recombinant cell expressing the olfactory receptor as mentioned above. Alternatively, an RTP1S variant polypeptide which has at least 80%, for example, 80% or higher, preferably 85% or higher, more preferably 90% or higher, still preferably 95% or higher, even more preferably 98% or higher, still even more preferably 99% or higher amino acid sequence identity to the human RTP1S variant consisting of the amino acid sequence represented by SEQ ID NO: 8 or the mouse RTP1S and promotes the expression of the olfactory receptor on the cell membrane may also be used instead of the human RTP1S in the preparation of the recombinant cell expressing the olfactory receptor as mentioned above.

According to the method of the present invention, the response of the olfactory receptor OR5K1 to Furaneol is measured following the addition of the test substance and Furaneol to the olfactory receptor. This measurement can be performed by an arbitrary method known in the art as a method for measuring the response of the olfactory receptor, for example, the measurement of an intracellular cAMP level. For example, the olfactory receptor, when activated by an odor molecule, is known to be conjugated with intracellular Gαs to activate adenylate cyclase, thereby increasing intracellular cAMP levels (Mombaerts P. Nat Neurosci. 5, 263-278). Thus, the intracellular cAMP level after the addition of the odor molecule can be used as an index for measuring the response of the olfactory receptor. Examples of methods for measuring the cAMP level include ELISA and reporter gene assay. Another example of the method for measuring the response of the olfactory receptor includes calcium imaging.

Subsequently, the effect of the test substance on the response to Furaneol is evaluated on the basis of the measured response of the olfactory receptor to identify a test substance inhibiting the response. The evaluation on the effect of the test substance can be conducted, for example, by comparing the responses of the receptor to Furaneol measured in the presence of various concentrations of the test substance. As a more specific example, the responses of the receptor to Furaneol are compared between a group supplemented with a higher concentration of the test substance and a group supplemented with a lower concentration of the test substance, between a group supplemented with the test substance and a group non-supplemented with the test substance, between a group supplemented with the test substance and a group supplemented with a control substance, or between before and after the addition of the test substance. When the addition of the test substance or the addition of a higher concentration of the test substance inhibits the response of the receptor, this test substance can be identified as a substance inhibiting the response of the olfactory receptor to Furaneol.

In the method of the present invention, a polypeptide having a function equivalent to OR5K1 can be used as the olfactory receptor instead of OR5K1. Examples of the polypeptide include a polypeptide which consists of an amino acid sequence having at least 80%, for example, 80% or higher, preferably 85% or higher, more preferably 90% or higher, still preferably 95% or higher, even more preferably 98% or higher, still even more preferably 99% or higher sequence identity to the amino acid sequence (SEQ ID NO: 2) of OR5K1 and is responsive to Furaneol.

Alternatively, in the method of the present invention, OR5K1 mentioned above as the olfactory receptor and polypeptides having a function equivalent thereto may each be used alone or may be used in combination of any two or more thereof.

The test substance identified by the above procedures is a substance which can inhibit the individual's perception of an odor caused by Furaneol by inhibiting the response of the olfactory receptor to Furaneol. Thus, the test substance identified by the above procedures is selected as an inhibitor of an odor caused by Furaneol. For example, when the receptor response in a test substance-supplemented group measured by the above procedures is reduced to preferably 60% or less, more preferably 50% or less, further preferably 25% or less of that in a test substance-non-supplemented group (e.g., the above-mentioned group non-supplemented with the test substance, group supplemented with a control substance, or before the addition of the test substance), the test substance can be selected as an inhibitor of an odor caused by Furaneol.

The substance selected by the method of the present invention can inhibit the odor caused by Furaneol, by olfactory masking based on the inhibition of the response of the olfactory receptor to Furaneol.

Thus, in one embodiment, the substance selected by the method of the present invention can serve as an active ingredient in an inhibitor of an odor caused by Furaneol. Alternatively, the substance selected by the method of the present invention can be contained as an active ingredient for inhibiting an odor caused by Furaneol in a compound or a composition for inhibiting an odor caused by Furaneol. Alternatively, the substance selected by the method of the present invention can be used for production of an inhibitor of an odor caused by Furaneol or for production of a compound or a composition for inhibiting an odor caused by Furaneol.

In one embodiment, the substance selected by the method of the present invention can be used as an active ingredient for inhibiting an odor caused by Furaneol, for example, a caramel aroma, a burnt sugar smell, or an unpleasant smell (e.g., a burnt sugar smell) generated by the application of a self-tanning agent to the skin or upon application of a product containing DHA.

In one embodiment, the substance selected by the method of the present invention can be used as an active ingredient for inhibiting an odor caused by Furaneol in every compound or composition desired to inhibit an odor caused by Furaneol or in every environment desired to inhibit an odor caused by Furaneol. Alternatively, the substance selected by the method of the present invention can be used as an active ingredient for inhibiting an odor caused by Furaneol, for production of a compound or a composition desired to inhibit an odor caused by Furaneol. Examples of the compound or the composition desired to inhibit an odor caused by Furaneol include skin tanning agents (also called self-tanning agents or sunless tanning agents), for example, a skin tanning agent containing DHA as a coloring agent and other skin tanning agents which employ browning reaction, and other products containing DHA. Furaneol excessively contained in a food or a drink may work as an off-flavor. For example, the presence of excessive Furaneol in powdered milk reduces its flavor or taste. Thus, other examples of the compound or the composition desired to inhibit an odor caused by Furaneol include foods or drinks desired to reduce the odor of Furaneol and compositions containing the foods or the drinks.

The following composition, production method, use, or method will be further disclosed herein as an exemplary embodiment of the present invention. However, the present invention is not intended to be limited by these embodiments.

<1> A method for searching for an inhibitor of an odor caused by Furaneol, comprising:
adding a test substance and Furaneol to an olfactory receptor OR5K1 or a polypeptide having at least 80% amino acid sequence identity thereto;
measuring the response of the olfactory receptor or the polypeptide to Furaneol; and
identifying a test substance inhibiting the response of the olfactory receptor or the polypeptide, on the basis of the measured response.

<2> The method according to <1>, wherein the olfactory receptor OR5K1 is a protein consisting of the amino acid sequence represented by SEQ ID NO: 2.

<3> The method according to <1> or <2>, wherein the polypeptide having at least 80% amino acid sequence identity to the olfactory receptor OR5K1 is a polypeptide having preferably at least 85%, more preferably at least 90%, still preferably at least 95%, even more preferably at least 98%, still even more preferably at least 99% amino acid sequence identity to the olfactory receptor OR5K1.

<4> The method according to any one of <1> to <3>, wherein the polypeptide having at least 80% amino acid sequence identity to the olfactory receptor OR5K1 is a polypeptide which has preferably at least 85%, more preferably at least 90%, still preferably at least 95%, even more preferably at least 98%, still even more preferably at least 99% amino acid sequence identity to the olfactory receptor OR5K1 and is responsive to Furaneol.

<5> The method according to any one of <1> to <4>, wherein, preferably, the olfactory receptor OR5K1 or the polypeptide having at least 80% amino acid sequence identity thereto is expressed on a recombinant cell genetically engineered to express the olfactory receptor or the polypeptide.

<6> The method according to <5>, wherein, preferably, the recombinant cell is the following cell:
a cell cotransfected with a gene of the olfactory receptor or the polypeptide and an RTP1S gene;
a cell cotransfected with a gene of the olfactory receptor or the polypeptide and RTP1S and RTP2 genes;
a cell cotransfected with a gene of the olfactory receptor or the polypeptide and a gene encoding a polypeptide which consists of an amino acid sequence having at least 78%, preferably 80% or higher, more preferably 85% or higher, still preferably 90% or higher, even more preferably 95% or higher, still even more preferably 98% or higher, further preferably 99% or higher sequence identity to the amino acid sequence represented by SEQ ID NO: 4 and promotes the expression of the olfactory receptor on the membrane, as with human RTP1S; or
a cell cotransfected with a gene of the olfactory receptor or the polypeptide and a gene encoding a human RTP1S variant.

<7> The method according to <5> or <6>, wherein, preferably, cultures of the recombinant cell are used as the olfactory receptor OR5K1 or the polypeptide having at least 80% amino acid sequence identity thereto.

<8> The method according to any one of <1> to <7>, preferably further comprising measuring the response of the olfactory receptor or the polypeptide in the absence of the test substance.

<9> The method according to <8>, preferably further comprising the following:
when the response of the olfactory receptor or the polypeptide in the presence of the test substance is reduced compared with the response of the olfactory receptor or the polypeptide in the absence of the test substance, the test substance is identified as a substance inhibiting the response of the receptor or the polypeptide to Furaneol.

<10> The method according to <8>, preferably further comprising the following:

when the response of the olfactory receptor or the polypeptide in the presence of the test substance is reduced to preferably 60% or less, more preferably 50% or less, further preferably 25% or less, of the response of the olfactory receptor or the polypeptide in the absence of the test substance, the test substance is identified as a substance inhibiting the response of the olfactory receptor or the polypeptide to Furaneol.

<11> The method according to any one of <1> to <10>, wherein the step of measuring the response of the olfactory receptor or the polypeptide is the measurement of an intracellular cAMP level by ELISA or reporter gene assay, or calcium imaging.

EXAMPLES

Hereinafter, the present invention will be described more specifically with reference to Examples.

Example 1

Identification of Olfactory Receptor Responding to Furaneol

1) Cloning of Human Olfactory Receptor Gene

On the basis of sequence information registered in GenBank, each human olfactory receptor gene was cloned by PCR with Human Genomic DNA Female (G1521: Promega Corp.) as a template. Each gene thus amplified by PCR was inserted into a pENTR vector (Invitrogen Corp.) according to the manual. A NotI-AscI site present on the pENTR vector was recombined into a NotI-AScI site prepared downstream of a Flag-Rho tag sequence on a pME18S vector.

2) Preparation of pME18S-Human RTP1S Vector

A human RTP1S gene (SEQ ID NO: 3) encoding human RTP1S (SEQ ID NO: 4) was inserted into the EcoRI-XhoI site of the pME18S vector.

3) Preparation of Olfactory Receptor-Expressing Cell

HEK293 cells expressing each of 400 types of human olfactory receptors were prepared. Each reaction solution having the composition shown in Table 1 was prepared, then left standing for 15 minutes in a clean bench, and then added to each well of a 96-well plate (Becton, Dickinson and Company). Subsequently, the HEK293 cells ($3 \times 10^5$ cells/cm$^2$) were inoculated thereto at 100 µL/well and then cultured at 37° C. for 24 hours in an incubator kept at 5% $CO_2$.

TABLE 1

| | |
|---|---|
| OPTI-MEM (GIBCO) | 50 µL |
| Human olfactory receptor gene (inserted to N-terminally Flag-Rho-tagged pME18S vector) | 0.075 µg |
| pGL4.29 (fluc2P-CRE-hygro, Promega) | 0.03 µg |
| pGL4.75 (hRluc-CMV, Promega) | 0.03 µg |
| pME18S-human RTP1S vector | 0.03 µg |
| lipofectamine 2000 (Invitrogen) | 0.4 µL |

4) Luciferase Assay

The olfactory receptors expressed on the HEK293 cells are conjugated with intracellular Gαs to activate adenylate cyclase, thereby increasing intracellular cAMP levels. In this study, their responses to Furaneol were measured using luciferase reporter gene assay which involved monitoring increase in intracellular cAMP level as luminescence intensity derived from a firefly luciferase gene (fluc2P-CRE-hygro). In addition, the cells were cotransfected with the reporter gene and a fusion gene (hRluc-CMV) of a Renilla luciferase gene downstream of a CMV promoter for use as an internal standard for correcting transfection efficiency or an error in the number of cells.

A medium was removed from the cultures prepared in the preceding paragraph 3). To the resulting cultures, 75 µL of a solution containing Furaneol (3 mM) prepared with a CD293 medium (Invitrogen Corp.) was added. The cells were cultured for 2.5 hours in a $CO_2$ incubator to express the luciferase genes at sufficient levels in the cells. The luciferase activity was measured using Dual-Glo™ luciferase assay system (Promega Corp.) according to the instruction manual of the product. Firefly luciferase-derived luminescence intensity induced by stimulation with Furaneol was divided by luminescence intensity in the cells without Furaneol stimulation to calculate a value as fold increase, which was in turn used as an index for response intensity.

5) Results

As a result of measuring the responses of 400 types of olfactory receptors to Furaneol (3 mM), only the olfactory receptor OR5K1 exhibited a response to Furaneol (FIG. 1). OR5K1 is a novel Furaneol receptor which has not been found so far to respond to Furaneol.

Example 2

Concentration-Dependent Response of OR5K1 to Furaneol

The olfactory receptor OR5K1 (SEQ ID NO: 2) was expressed, together with human RTP1S (SEQ ID NO: 4), on HEK293 cells by the same procedures as in Example 1 and then examined for the concentration dependence of its response to varying concentrations of Furaneol (0, 3, 10, 30, 100, 300, 1000, and 3000 µM). As a result, OR5K1 exhibited a concentration-dependent response to Furaneol (FIG. 2).

Example 3

Identification of OR5K1 Antagonist 84 types of test substances were examined for their antagonistic activity against the response of the olfactory receptor OR5K1 to Furaneol.

Furaneol (3 mM) and each test substance (100 µM) were added to HEK293 cells allowed to express the olfactory receptor OR5K1 by the same procedures as in Example 2. The response of the olfactory receptor was measured to evaluate change in receptor response caused by the addition of the test substance.

The rate of inhibition of the receptor response by the test substance was calculated as follows: firefly luciferase-derived luminescence intensity (Y) in the olfactory receptor OR5K1-expressing cells without Furaneol stimulation was subtracted from firefly luciferase-derived luminescence intensity (X) induced by stimulation with Furaneol alone to determine receptor activity (X−Y) based on the stimulation with Furaneol alone. Likewise, the luminescence intensity (Y) in the cells without Furaneol stimulation was subtracted from luminescence intensity (Z) induced by stimulation with the mixture of Furaneol and the test substance to determine receptor activity (Z−Y) in the presence of the test substance. The rate of reduction in the receptor activity (Z−Y) in the presence of the test substance with respect to the receptor activity (X−Y) based on the stimulation with Furaneol alone was calculated according to an expression shown below to determine the rate of inhibition of the receptor response by the test substance. In this assay, a plurality of independent duplicate experiments were performed. An average of the experiments in each run was obtained.

Rate of inhibition (%)=$\{1-(Z-Y)/(X-Y)\} \times 100$

As a result, 17 types of test substances had 40% or higher rate of inhibition of the response of OR5K1 to Furaneol (reduced the response to 60% or less), demonstrating that these test substances have antagonistic activity against OR5K1 (Table 2).

TABLE 2

| | |
|---|---|
| 75% or more rate of inhibition (response was reduced to 25% or less; very strong antagonist) | ω-6-Hexadecenlactone (ambrettolide)<br>7-Acetyl-1,2,3,4,5,6,7,8-octahydro-1,1,6,7-tetramethyl-naphthalene (Iso E Super)<br>3-(4-tert-Butylphenyl)propanal (bourgeonal)<br>5-Methyl-2-(1-methylethyl)-phenol (thymol)<br>Oxacyclohexadecen-2-one (Habanolide(R))<br>(5E)-3-Methylcyclopentadec-5-en-1-one (Muscenone(R) Delta)<br>Citral<br>*Patchouli* oil<br>1-(5,6,7,8-tetrahydro-3,5,5,6,8,8-hexamethyl-2-naphthalenyl)-ethanone (Tonalid(R))<br>4,6,6,7,8,8-Hexamethyl-1,3,4,6,7,8-hexahydrocyclopenta[g]isochromene (galaxolide)<br>(E)-3-Methyl-4-(2,6,6-trimethylcyclohex-2-en-1-yl)but-3-en-2-one (methyl ionone-G)<br>Muscone<br>1-(2,3,4,7,8,8a-hexahydro-3,6,8,8-tetramethyl-1H-3a,7-methanoazulen-5-yl)-ethanone (acetylcedrene) |
| 50% or more rate of inhibition (response was reduced to 50% or less; strong antagonist) | Cedryl acetate<br>2-Ethyl-4-(2,2,3-trimethyl-3-cyclopenten-1-yl)-2-buten-1-ol (bangalol) |
| 40% or more rate of inhibition (response was reduced to 60% or less; weak antagonist) | Lemon oil<br>(1-Methyl-2-(1,2,2-trimethylbicyclo[3.1.0]-hex-3-ylmethyl)cyclopropyl)methanol (Javanol(R)) |

Example 4

Evaluation on Ability of OR5K1 Antagonist to Inhibit Odor of Furaneol

Each test substance having antagonistic activity against OR5K1, identified in Example 3, was confirmed by a sensory test for its ability to inhibit the odor of Furaneol.

Each panelist smelled 0.5 g of Furaneol (1%)-containing cloth supplemented with 0.5 μL of a flavor, and then evaluated the intensity of the odor of Furaneol compared with cloth non-supplemented with the flavor. The sensory evaluation test was conducted by 3 panelists. The odor of Furaneol was evaluated as 1 when strongly perceivable and as 5 when not perceivable.

Figure 3:
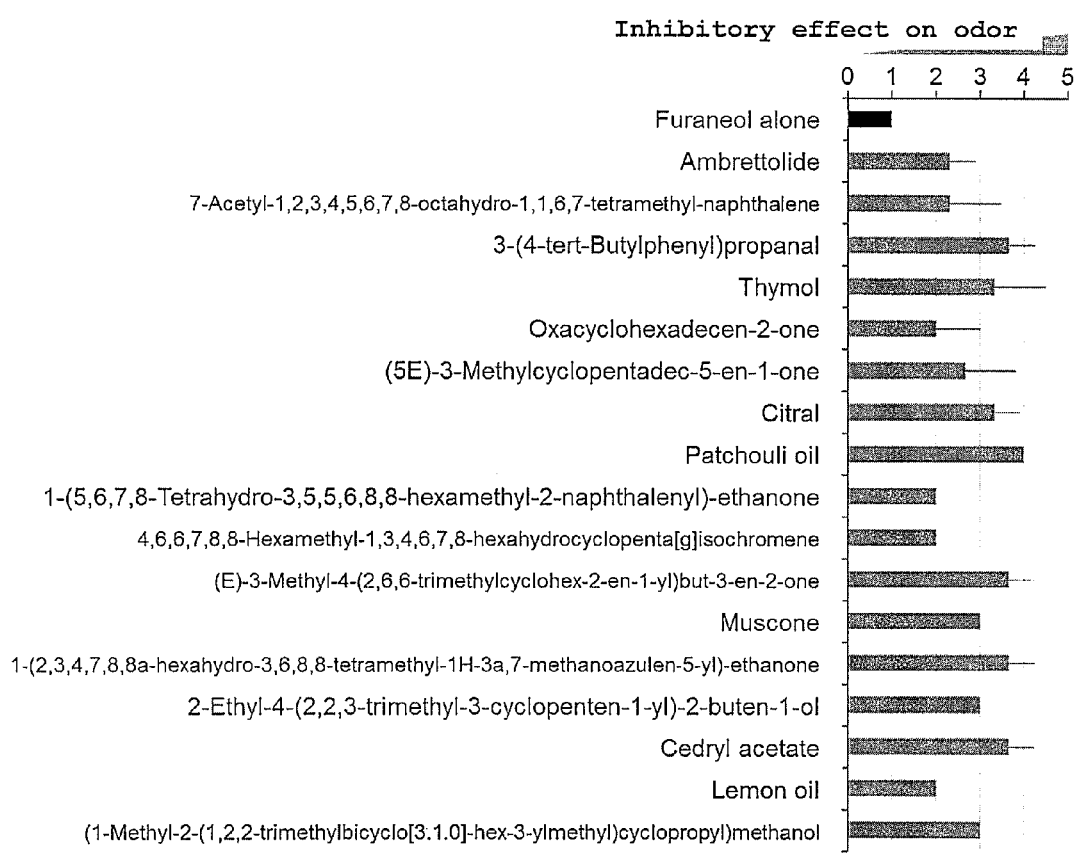
FIG. 3 shows results of sensory evaluation on the inhibitory effects of various compounds on the odor of Furaneol. n=3, error bar=±SE.

As a result, all the 17 types of test substances demonstrated to inhibit the response of OR5K1 to Furaneol in Example 3 inhibited the odor of Furaneol (FIG. 3).

The invention claimed is:

1. A method of screening for an inhibitor of an odor caused by 2,5-dimethyl-4-hydroxy-3(2H)-furanone, comprising:
    (1), adding a test substance and 2,5-dimethyl-4-hydroxy-3(2H)-furanone to a cultured cell expressing olfactory receptor OR5K1, wherein the amino acid sequence of olfactory receptor OR5K1 consists of the amino acid sequence of SEQ ID NO:2, or a polypeptide having at least 95% amino acid sequence identity thereto;
    (2) measuring the response of the olfactory receptor or the polypeptide to 2,5-dimethyl-4-hydroxy-3(2H)-furanone; and
    (3) identifying a test substance that inhibits the response measured in (2) as an inhibitor of the odor.

2. The method according to claim 1, wherein the cultured cell expresses olfactory receptor OR5K1 that has an amino acid sequence that consists of the amino acid sequence of SEQ ID NO: 2.

3. The method according to claim 1, wherein the polypeptide having at least 95% amino acid sequence identity to the olfactory receptor OR5K1 is a polypeptide which consists of an amino acid sequence having at least 95% identity to the amino acid sequence represented by SEQ ID NO: 2 and is responsive to 2,5-dimethyl-4-hydroxy-3(2H)-furanone.

4. The method according to claim 1, wherein the olfactory receptor OR5K1 or the polypeptide having at least 95% amino acid sequence identity thereto is expressed on a recombinant cell genetically engineered to express the olfactory receptor or the polypeptide.

5. The method according to claim 1, further comprising measuring the response of the olfactory receptor or the polypeptide in the absence of the test substance.

6. The method according to claim 5, wherein when the response of the olfactory receptor or the polypeptide in the presence of the test substance is reduced to 60% or less of the response of the olfactory receptor or the polypeptide in the absence of the test substance, the test substance is identified as a substance inhibiting the response of the olfactory receptor or the polypeptide to 2,5-dimethyl-4-hydroxy-3(2H)-furanone.

7. The method according to claim 1, wherein the step of measuring the response of the olfactory receptor or the polypeptide is the measurement of an intracellular cAMP level by ELISA or reporter gene assay, or calcium imaging.

8. The method according to claim 1, wherein the cultured cell expressing the olfactory receptor OR5K1 or the polypeptide having at least 95% amino acid sequence identity thereto is a recombinant cell genetically engineered to express the olfactory receptor or the polypeptide.

9. The method according to claim 1, wherein the cultured cell expresses a polypeptide having at least 95% amino acid sequence identity to the olfactory receptor OR5K1.

10. The method according to claim 9, wherein the polypeptide has at least 98% amino acid sequence identity to olfactory receptor OR5K1.

11. The method according to claim 10, wherein the polypeptide has at least 99% amino acid sequence identity to olfactory receptor OR5K1.

* * * * *